US011659982B2

(12) United States Patent
Ulmschneider et al.

(10) Patent No.: US 11,659,982 B2
(45) Date of Patent: May 30, 2023

(54) INSTRUMENT SHAFT WITH SEVERAL CHANNELS AND ITS MANUFACTURE

(71) Applicant: KARL STORZ SE & Co. KG, Tuttlingen (DE)

(72) Inventors: Daniel Ulmschneider, Tuttlingen (DE); Andreas Limberger, Tuttlingen (DE); Christian Czupalla, Tuttlingen (DE); Kamilla König-Urban, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 24 days.

(21) Appl. No.: 16/902,555

(22) Filed: Jun. 16, 2020

(65) Prior Publication Data

US 2020/0397237 A1    Dec. 24, 2020

(30) Foreign Application Priority Data

Jun. 19, 2019    (DE) .................... 10 2019 116 583.0

(51) Int. Cl.
*A61B 1/018* (2006.01)
*A61B 1/00* (2006.01)
(Continued)

(52) U.S. Cl.
CPC ............ *A61B 1/018* (2013.01); *A61B 1/0011* (2013.01); *A61B 1/00066* (2013.01); *A61B 1/05* (2013.01);
(Continued)

(58) Field of Classification Search
CPC ... A61B 1/018; A61B 1/00066; A61B 1/0011; A61B 1/05; A61B 1/0684; A61B 1/128;
(Continued)

(56) References Cited

U.S. PATENT DOCUMENTS 10,080,824 B2    9/2018  Dillon
2005/0154262 A1*  7/2005  Banik .................. A61B 1/0676
600/179

(Continued)

FOREIGN PATENT DOCUMENTS

EP    2294967 A1    3/2011

OTHER PUBLICATIONS

European Search Report for European Application No. 20180638.7, dated Nov. 19, 2020.
(Continued)

*Primary Examiner* — Aaron B Fairchild
(74) *Attorney, Agent, or Firm* — Jason H. Vick; Sheridan Ross, PC (57) ABSTRACT

A medical instrument for providing access to the interior of the body comprises a shaft having an elongated base body and a handle. The base body extends between a distal end and a proximal end of the shaft. The handle is coupled to the base body of the shaft at the proximal end. The shaft defines at least a first channel and a second channel that extend through the shaft. The first channel provides a passage for surgical instruments through the shaft. The second channel is adapted to accommodate an observation optics. The second channel is adjacent to at least one secondary channel that is connected to the second channel.

20 Claims, 6 Drawing Sheets

(51) Int. Cl.
  *A61B 1/05* (2006.01)
  *A61B 1/12* (2006.01)
  *A61B 17/34* (2006.01)
  *A61B 1/06* (2006.01)
  *B33Y 80/00* (2015.01)
(52) U.S. Cl.
  CPC ............ *A61B 1/0684* (2013.01); *A61B 1/128* (2013.01); *A61B 17/3423* (2013.01); *B33Y 80/00* (2014.12); *A61B 2560/0406* (2013.01)
(58) Field of Classification Search
  CPC ........ A61B 17/3423; A61B 2560/0406; A61B 1/00073; A61B 1/051; A61B 1/00135; A61B 1/00119; B33Y 80/00
  USPC ........................................................ 600/175
  See application file for complete search history.

(56) References Cited

U.S. PATENT DOCUMENTS

| | | | |
|---|---|---|---|
| 2007/0106122 A1 | 5/2007 | Yokota et al. | |
| 2007/0293726 A1* | 12/2007 | Goldfarb | A61B 1/233 600/178 |
| 2008/0151046 A1* | 6/2008 | Scott | A61B 1/12 348/82 |
| 2008/0255424 A1* | 10/2008 | Durgin | A61B 90/98 600/156 |
| 2010/0160813 A1* | 6/2010 | Ohno | A61B 1/00105 600/562 |
| 2011/0065985 A1 | 3/2011 | Wehrheim | |
| 2011/0306834 A1* | 12/2011 | Schrader | G02B 23/2484 600/109 |
| 2013/0172673 A1 | 7/2013 | Kennedy, II et al. | |
| 2014/0316211 A1* | 10/2014 | Hermle | A61B 17/00008 600/210 |
| 2014/0336456 A1* | 11/2014 | Demers | A61B 1/00133 600/137 |
| 2016/0030707 A1* | 2/2016 | Dillon | A61B 1/015 604/537 |
| 2017/0189053 A1* | 7/2017 | Otsubo | A61B 17/32053 |
| 2019/0117047 A1 | 4/2019 | Huang et al. | |
| 2020/0113698 A1* | 4/2020 | Herzog | B22F 10/66 |
| 2020/0154981 A1* | 5/2020 | Mankowski | A61B 1/0669 |

OTHER PUBLICATIONS

Search Report for German Application No. 10 2019 116 583.0, dated Feb. 28, 2020.

* cited by examiner

INSTRUMENT SHAFT WITH SEVERAL CHANNELS AND ITS MANUFACTURE

CROSS-REFERENCE TO RELATED APPLICATIONS

This application claims priority from German patent application 10 2019 116 583.0, filed on Jun. 19, 2019. The entire content of that priority application is incorporated herein by reference.

BACKGROUND

The present disclosure relates to medical instruments and components, for example to those that are used to provide access to the interior of the body, and their manufacture. In certain embodiments, but not limited thereto, the present disclosure relates to a spatula for an endoscopic instrument, for instance to a spatula for a mediastinoscope, for example in the form of a video mediastinoscope.

The present disclosure relates to medical instruments and components used to provide access to the interior of the body for a surgeon or other medical personnel, such as instruments for minimally invasive surgery and/or endoscopy. Access to the interior of the body may be provided through natural or artificially created openings.

At least in exemplary embodiments relates to the present disclosure on instruments and devices for mediastinoscopy. However, the disclosure is not exclusively limited thereto. By way of example, instruments for thoracic surgery in general or endoscopic instruments in general may be involved.

U.S. 2007/0106122 A1 discloses an intubation assistance apparatus for use in inserting a distal end of an intubation tube into a target site such as a trachea of a patient. The intubation assistance apparatus includes a main body, an insertion instrument having an elongated insertion section for insertion into a trachea or its vicinity of a patient from a mouth cavity of the patient, and an imaging device for acquiring an image of an observation site at a distal end portion of the insertion instrument as an electronic image.

More generally, the present disclosure relates to the disclosure on those endoscopic devices and assemblies that provide several channels in a shaft. For example, the at least two channels are a first channel for providing a passage for a surgical instrument or the like, and a second channel for receiving an observation optics. The second channel can also accommodate illumination optics in addition to the observation optics. It is also conceivable to provide at least one separate channel for the illumination optics. It is also conceivable to use channels for the supply and/or removal of fluids (such as insufflation gas, flushing liquids or the like). The subdivision of such probe-like instruments into several channels simplifies operation and handling, as it facilitates cleaning, for example. Furthermore, by way of example, the observation optics in the respectively assigned channel is sufficiently mechanically protected so that manipulations/movements in the channel that is provided for the passage of surgical instruments do not have any adverse effects on the illumination optics.

At least in exemplary arrangements, that part of the instrument, which is actually inserted into the interior of the body, is provided with a round, oval or even circular cross section. This is not to be understood as a limitation, but the object is usually to achieve the most compatible external shape possible in order to minimize any trauma for the patient or, in general, the stress during the medical procedure. Therefore, one object is to keep the diameter and/or the cross-sectional surface of such a tube part as small as possible Further challenges arise from the desired provision of image signals. This includes in exemplary embodiments the provision of an observation optics, which is coupled with an image acquisition unit (image sensor), so that a direct or indirect reproduction of the field of view (in the body) is possible. In exemplary arrangements, this includes a distal arrangement of the observation optics and the image acquisition unit (distal at the tube part). The image acquisition unit comprises one or more image sensors and other electronic components. The image acquisition unit provides an electronic (digital) image signal, which is picked off at the proximal end of the tube part. The observation optics is regularly supplemented by an illumination unit.

The illumination unit and the image acquisition unit generally cause a certain heat input into the instrument and immediately into the patient. In this context, it is also important to avoid excessive loads. Accordingly, excess heat must be dissipated.

For the purposes of the present disclosure, the term distal relates to the section/region of the instrument that is facing away from the user. In other words, a distal end of the instrument is regularly inserted into the interior of the body during the medical procedure, at least for endoscopic instruments. In the context of this disclosure, the term proximal refers to a section/region of the instrument that is facing away from the distal end and facing the user. Thus, an instrument with a shaft-shaped tube part includes, for example, a tubular body that extends between a distal and a proximal end. This may include arrangements, in which the distal end is inside the body and the proximal end is outside the body during the medical procedure. However, this is not to be understood to be limiting.

The manufacture of shafts/tube bodies for tube parts of surgical instruments often requires great effort due to various boundary conditions, for instance if several channels are provided. On the one hand, challenges arise from miniaturization. Furthermore, good and easy cleaning and/or reprocessing (sterilization, etc.) is often required. Furthermore, the materials used should be suitable for medical applications.

In view of this, it is an object of the present disclosure to present a medical instrument for providing an access to the interior of the body with a shaft having at least a first channel and a second channel.

It is a further object of the present disclosure to present a medical instrument that provides the required functions and that has a design that is suitably adapted to the required functional spectrum. This may also include adequate handleability and maneuverability.

It is a further object of the present disclosure to present a suitable method for the manufacture of such an instrument.

It is a further object of the present disclosure to present a manufacturing method that uses a process suitable for this specific purpose, so that at least two channels are provided for a given cross section of the shaft and, if necessary, further functions can be integrated.

It is a further object of the present disclosure to present a manufacturing method that can be carried out in as few steps as possible and that allows a design that is adapted to the intended use, for instance with regard to cleaning and reprocessing of the instrument.

It is a further object of the present disclosure to present a manufacturing method for cost-efficient manufacture, for instance with regard to additional manual operations.

It is a further object of the present disclosure to present a manufacturing method that is reproducible and reliable.

It is further object of the present disclosure to present a medical instrument that can be equipped with powerful image sensors and similar components, wherein waste heat from such components can be efficiently removed.

SUMMARY

In regard of the medical instrument, these and other objects are achieved by a medical instrument for providing access to the interior of the body, for instance a spatula for an endoscopic instrument, the instrument comprising:
- a shaft having an elongated base body, wherein the base body extends between a distal end and a proximal end of the shaft,
- a handle that is coupled to the base body of the shaft at its proximal end,
- wherein the shaft defines at least a first channel and a second channel that are extending through the shaft,
- wherein the first channel provides a passage for surgical instruments through the shaft,
- wherein the second channel is adapted to accommodate an observation optics, and
- wherein the second channel is adjacent to at least one secondary channel that is connected to the second channel.

In this way, the design of the component allows efficient heat dissipation via at least one secondary channel. This enables the use of powerful image sensors and illumination units, which generate corresponding heat loss. The medical instrument may generally be referred to as medical apparatus or medical device.

By way of example, the base body is arranged as a slotted tube, for instance a continuous slotted tube. In this way, additional instruments can be easily inserted into the first channel.

It is understood that terms such as first channel and second channel are not to be understood as a qualitative distinction. The numbering used is primarily for differentiation purposes. The first channel may also be referred to as an instrument channel and/or instrument passage. The second channel may also be referred to as the observation channel. The at least one secondary channel may also be referred to as a cooling channel.

The secondary channel can be parallel to the second channel. However, this is not a necessary requirement. For example, if the base body that forms the shaft is tapered and the axes of the channels (possibly eccentrically arranged) follow this tapering, there may be adjacent but not strictly parallel arrangements of the channels.

At least in an exemplary embodiment, the second channel is provided within the first channel. It is also conceivable that the at least one secondary channel is formed within the first channel.

According to an exemplary embodiment, the base body of the shaft is designed integrally, wherein the base body is for instance produced by an additive manufacturing method. In other words, the base body can be designed in one piece. Preferably, the entire shaft is formed by the base body.

Overall, at least in exemplary embodiments, a configuration of the instrument is conceivable, which comprises the shaft and a handle for handling the shaft, wherein a connecting piece between the shaft and the handle is provided, if necessary. The handle can be designed as a handle grip, by way of example. In principle, the handle can also be part of a housing at the proximal end of the shaft. The spatula-shaped shaft is guided via the handle.

Additive manufacturing allows the formation of several channels in a single-piece component, wherein the channels can be coupled together, as required. By way of example, such connections cannot be produced with conventional manufacturing processes for one-piece components, or only at huge expenses.

Since it is possible to introduce additional secondary channels into the shaft of the instrument, heat dissipation can be improved, for example. This makes it possible to install more powerful observation optics, illumination units and (electronic) image sensors. Since the heat can now be efficiently dissipated, the stress for the patient is not increased.

The design of the shaft and/or its base body can be adapted to the anatomical conditions. By way of example, channels lying one inside the other can be realized, wherein constrictions, inner edges, chamfers and similar problematic design elements can be avoided. Surfaces can be designed to be round and provided smooth transitions. Benefits result, for example, in the cleaning and/or reprocessing of the instrument. The better the elements are accessible during cleaning, the less effort is required.

The integral, one-piece design, which also includes the formation of the channels, also ensures that the time and effort required for processing is reduced, for instance with regard to the individual processing steps. In an ideal case, no comprehensive mechanical machining is necessary. This is not to be understood as limiting. In individual cases, for example, it may very well be possible to carry out subsequent machining to improve surface properties. Even if the step of additive manufacturing takes a certain amount of time, a reduction of the manufacturing time may overall be achieved.

A further potential advantage is that the costs for specific manufacturing equipment for the manufacture of the shaft can be reduced. Ideally, the entire shape of the base body of the shaft can be produced in just one operation, supplemented by a few finishing operations, if necessary.

The one-piece design may have the further potential advantage that the entire shaft and/or its base body can be made of one and the same material. By way of example, materials with favorable properties in terms of biocompatibility and/or patient compatibility can be selected. For example, austenitic, stainless steel materials are suitable. Furthermore, additive manufacturing potentially has advantages with regard to the actual material consumption.

The base body to be produced can be specifically adapted to expected loads. There are only a few design restrictions. The component to be produced can be reinforced specifically at potentially highly stressed points. Less stressed areas can be thinner/lighter.

In the case of components designed in one piece, additive manufacturing allows the integration of through holes, blind holes and, by way of example, connections provided therebetween. Both blind holes and cross-connections between individual channels can only be realized at great expenses, if at all, with conventional manufacturing approaches for single-piece components.

According to another exemplary embodiment of the instrument, the base body is at least sectionally slotted. Preferably, the base body is completely slotted along its longitudinal extension between the distal and the proximal end. The slotted design of the base body is possible without subtractive measures. With additive manufacturing, the corresponding space is just omitted when joining/cross-linking the particles.

It is also possible to reinforce specific sections of the component so that sufficient structural stability is provided, despite the continuous design of the slot. The slot allows lateral access to the first channel, for instance radial access. In this way, further instruments can be easily inserted laterally into the first channel.

According to another exemplary embodiment of the instrument, the second channel accommodates besides the observation optics also an illumination unit. The illumination unit comprises, for example, a light guide extending from the proximal end of the shaft to the distal end. In principle, it is also conceivable, as an alternative to the light guide or in addition to it, to use at least one LED or similar light sources directly in the second channel. Generally, the illumination unit may also include an illumination optic.

In other words, the observation optics and the illumination unit share the available space in the second channel. It is conceivable to subdivide the second channel in the desired way by (inner) shafts inserted therein. The inner shafts each provide a receptacle for the observation optics and the illumination unit, respectively, and, if necessary, a boundary therebetween.

According to another exemplary embodiment of the instrument, the second channel is connected to the at least one secondary channel via a connection channel. It is understood that several connection channels are also conceivable.

For example, such a connection channel is designed as a cross connection (essentially transverse to the longitudinal extension of the shaft). The formation of the connection channel is not possible with conventional manufacturing methods or only possible at great expenses.

The at least one connection channel can be used to improve heat dissipation. For example, the at least one connection channel can be coupled to a heat-loaded region of the second channel. For example, the at least one connection channel is arranged adjacent to the distal end of the base body and/or in a distal end region of the base body. Furthermore, the at least one connection channel is filled, for example, with a material that dissipates heat considerably well (material with good thermal conductivity). In this way, heat can be dissipated specifically from the second channel in the direction of the at least one secondary channel. This means that the waste heat does not have to be dissipated, or not completely, via the second channel itself.

In this way, components with high power loss can be arranged at the distal end of the base body. By way of example, this may involve considerably powerful image sensors with appropriate electronics, which capture images provided by observation optics and convert them into digital information.

According to another exemplary embodiment of the instrument, the connection channel is located in a distal end region or adjacent to it. In general, it is conceivable that the connection channel is located near heat generating and/or heat dissipating components in the second channel.

According to another exemplary embodiment of the instrument, the at least one secondary channel is designed as a blind hole and closed at the distal end of the shaft. This may have the potential advantage that the at least one secondary channel is safely sealed towards the distal end of the shaft. This makes it more difficult for media to pass through the at least one secondary channel. By way of example, the blind hole design includes a design without countersink. In other words, at least in exemplary embodiments, the blind hole can have a flat bottom towards the distal end of the shaft.

According to another exemplary embodiment of the instrument, the at least one secondary channel accommodates a heat removal element to dissipate heat from the distal end to the proximal end. In general, this is an element made of a material with good thermal conductivity. In principle, it is also conceivable to provide a heat removal element, which can be flown through.

According to another exemplary embodiment of the instrument, the second channel is located between two secondary channels, which connect a distal end region of the channel to the proximal end of the instrument.

In an exemplary arrangement, where the second channel is formed in the first channel, the two secondary channels are arranged on both sides of the second channel, so that overall the installation space available for the first channel (for the open cross section available there for the passage) is not excessively reduced. In other words, the two secondary channels can be arranged in the region, in which, in conventional manufacture with two tube bodies arranged one inside the other, there would be a chamfer/inner edge between the tubular body of the second channel and the peripheral wall of the first channel. This means that for a given outer dimension of the base body, there are no major restrictions for the operator with regard to the passage that is provided in the first channel for instruments and the like. It is also conceivable to provide further secondary channels. The additive manufacturing provides great freedom of design here.

According to another exemplary embodiment of the instrument, the first channel comprises a kidney-shaped cross section. This applies for instance to the passage formed in the first channel. According to this embodiment, the second channel is adjacent to a concave section of the kidney-shaped cross-section. The kidney-shaped cross-section comprises convex (outwardly curved) sections and a concave (inwardly curved) section on one side. This definition refers to the provided passage/recess. If this definition is reversed, with reference to the wall, an inverse assignment of the convex/concave sections can also be applied.

The kidney-shaped cross-section resembles an oval or elongated hole having a short main axis and a long main axis, wherein along the long main axis one of the two outer sides is provided with the concave (inwardly curved) section. Preferably the cross-section comprises round, in particular tangential transitions. In this way, edges, corners, bottlenecks and the like can be avoided.

According to another exemplary embodiment, the second channel is provided with a circular cross section and is indented in an imaginary oval of the first channel to form the kidney-shaped cross section.

According to another exemplary embodiment of the instrument, the second channel, viewed in a cross-sectional direction of the shaft, is located between the first channel and the handle, wherein the at least one secondary channel is located laterally of an imaginary longitudinal central plane through the shaft. This may be the case for both secondary channels. The imaginary longitudinal central plane is defined by a center (e.g. intersection of the two major axes) of the first channel and a center of the second channel. By way of example, the longitudinal central plane forms a symmetry axis of the shaft. The longitudinal central plane is also an example of an axis of symmetry of the handle. The lateral slot in the shaft is offset from the imaginary longitudinal central plane, in particular provided in a region of the cladding (circumferential wall) of the first channel, which is facing away from it.

According to another exemplary embodiment of the instrument, the base body of the shaft comprises an accumulation of material at its circumferential region that is facing the handle (hand grip), which accommodates the second channel and the at least one secondary channel. The additive manufacturing process allows, within wide limits, any wall thickness when forming the base body. In this way, the material accumulation can be formed without much additional effort. Accordingly, sufficient material is available to form there the second channel and the at least one secondary channel. Furthermore, the material accumulation has a favorable moment of resistance (against bending and the like), so that the stability of the base body and the shaft is increased overall. In this way, for example, the lateral slot can be arranged to be continuous, so that an open profile results for the first channel. Nevertheless, the shaft is sufficiently strong.

According to a further exemplary embodiment of the instrument, the base body tapers from the proximal end towards the distal end of the at least sectionally, wherein for instance the base body tapers continuously. In this way, the shaft can be inserted more easily. Here, too, additive manufacturing allows application-specific design within wide limits.

According to a further exemplary embodiment of the instrument, a tip is formed at the distal end of the shaft of the base body, which is formed by an oblique section of the base body, for instance. Thus the tip is shaped like a tongue or trough. In this way, the instrument can be adapted to the conditions of use without great additional effort through additive manufacturing.

According to another exemplary embodiment of the instrument, the second channel accommodates in its distal end region a lens assembly, which is located in front of an image sensor. The at least one secondary channel allows an efficient heat dissipation, also of components located in the distal region, so that the distal arrangement of powerful image sensors and lens assemblies as well as corresponding elements for illumination of the field of view is possible.

According to a further exemplary embodiment of the instrument, the at least one secondary channel is adapted to dissipate waste heat from the image sensor or the lens assembly and is, in certain embodiments, coupled laterally to the distal end region via the connection channel.

The at least one image sensor is exemplarily part of an image acquisition unit, which comprises one or more image sensors. In this way, an observation channel or even two observation channels (stereo observation) can be implemented. The image sensors can be formed by CCD sensors, for example. Furthermore, control circuits and similar components can be located directly at the distal end of the shaft.

In regard of the manufacturing method, the above and other objects are achieved by a method for manufacturing a medical instrument for providing access to the interior of the body, for instance a spatula for an endoscopic instrument, the method comprising the steps of:
providing a data embodiment of a shaft with an elongated base body,
wherein the base body extends between a distal end and a proximal end of the shaft,
wherein the shaft defines at least a first channel and a second channel extending through the shaft,
wherein the first channel provides a passage for surgical instruments through the shaft,
wherein the second channel being is arranged to accommodate an observation optics, and
wherein the second channel is adjacent to at least one secondary channel that is connected to the second channel,
integral manufacture of the shaft with the first channel, the second channel and the at least one secondary channel in an additive manufacturing method based on a powdery metallic basic material, while taking into account the data embodiment, and
connecting the shaft with a handle at the proximal end of the base body of the shaft.

Also in this way, the object of the disclosure is completely achieved.

The method is generally suitable for the manufacture of a component according to any one of the embodiments described above. The additive manufacturing allows a high degree of design freedom, so that the base body, possibly the entire shaft, can be designed completely or to a large extent integrally/in one-piece. Despite the integral design, various channels can be incorporated into the base body, and it is also possible to create cross-connections between the channels. This is also provided for channels that do not extend completely (as through holes) through the base body. Such channels (blind holes), which do not completely penetrate the base body, can also be connected to other channels in the immediate vicinity of the distal end, where the channels end blindly. This is not possible with conventional manufacturing methods or only with excessive effort.

The generation of slotted pipes and nested/interleaved channels is also easily possible through additive manufacturing. Furthermore, additive manufacturing allows smooth transitions between different design elements, which further simplifies cleaning/processing.

According to an exemplary embodiment of the method, the step of additive manufacturing of the shaft includes manufacturing on the basis of a powdery austenitic stainless steel material. Such a material is suitable for medical applications. There is therefore a good patient compatibility. Furthermore, such materials are suitable for cleaning/preparation between different applications. By way of example, the material can be a stainless steel with the material number 1.4404. Such stainless steels have a high corrosion resistance.

According to a further exemplary embodiment of the method, the manufacturing step comprises the use of a powder bed based device for additive manufacturing, wherein powder is softened and joined in a building space of the device by high-energy radiation. An SLM (selective laser melting) method can be used, by way of example. An SLS method (Selective Laser Sintering) is also conceivable. Both are so-called powder bed methods.

In the SLM method, the material is in powder form, wherein material is transferred from a storage chamber into a construction chamber and deposited there in layers, wherein a platform is provided in the construction chamber, which can be respectively lowered by the thickness of one layer. The uppermost layer in each case is at least partially melted with a laser beam so that a solid component with the desired geometry is produced layer by layer. Regions, in which the powder is not melted, are cleaned after the construction, so that the result is a largely or completely finished component with the desired cavities/channels.

According to another exemplary embodiment of the method, the base body is manufactured in an upright position, with vertical orientation of a longitudinal axis in relation to the building platform. Cross-sectional regions ("slices") of the base body are produced simultaneously or at least overlapping in time. In this way, sufficiently homogeneous properties are obtained in the respective cross-sectional region.

According to another exemplary embodiment of the method, the step of providing the data embodiment includes providing a data embodiment that anticipates an expected distortion of the component during manufacture. In other words, the warpage of the component can be predicted based on experience and/or simulations, so that the warpage can be "provided". If an artificially distorted component is used as a basis for manufacture and the expected distortion occurs, the result is the desired shape.

A data embodiment is a digital image of the shape of the component. The digital image can be supplemented by further manufacturing information. According to an exemplary embodiment of the method, a distortion resulting from inhomogeneous material distribution and/or material accumulation is taken into account when providing the data embodiment that anticipates the expected distortion.

According to a further exemplary embodiment, the method further comprises at least one material-removing post-processing step, which comprises a flow machining of at least the second channel. In flow machining (flow grinding), abrasive is driven by a fluid flow and moved along the workpiece. In this way, for example, the desired surface quality can be produced in the second channel. In principle, such a method is also conceivable for the first channel.

In exemplary embodiments, the at least one secondary channel is not flow machined, since the secondary channel is not designed as a through hole. If there is no likelihood of substances passing through the secondary channel in the direction of the interior of the body, surface qualities achievable with the additive method are sufficient here.

It is to be understood that the above-mentioned features of the present disclosure and those to be explained in the following can be applied not only in the respectively specified combination, but also in other combinations or singly, without departing from the scope of the present disclosure.

BRIEF DESCRIPTION OF THE DRAWINGS

Further features and advantages of embodiments in accordance with the present disclosure are disclosed by the following description of a plurality of exemplary embodiments, with reference to the drawings, wherein.

EMBODIMENTS

Figure 1:
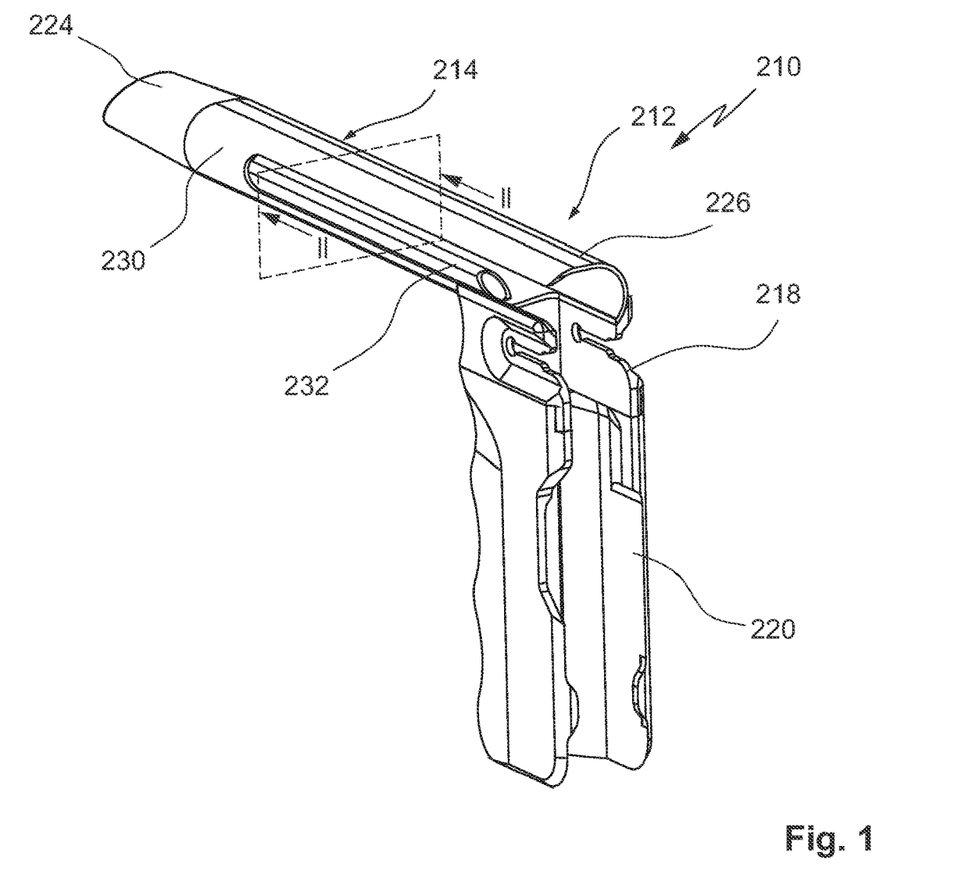
FIG. 1: is a perspective rear view of an arrangement of a medical instrument in the form of a video mediastinoscope.

FIG. 1 shows a conventional design of an instrument which is overall designated by 210, using a perspective rear view. By way of example, the instrument 210 is a mediastinoscope, for instance a video mediastinoscope.

The instrument 210 comprises a shaft-shaped spatula 212, which is formed by a shaft 214. The shaft 214 has a considerable longitudinal extension. In addition to the spatula 212, the instrument 210 comprises a handle 220 and a connecting piece 218 arranged therebetween, which provides an adapter between the spatula 212 and the handle 220. The shaft 214 forming the spatula 212 extends between a distal end 224 and a proximal end 226. In the exemplary operation as mediastinoscope, the distal end 224 is inserted into the interior of the patient's body. At the proximal end 226 of the shaft 214, the handle 220 couples to the shaft 214 via the connecting piece 218. The handle 220 is clearly inclined in relation to the longitudinal extension of the shaft 214 and is arranged similar to a pistol grip in the exemplary embodiment.

Figure 2:
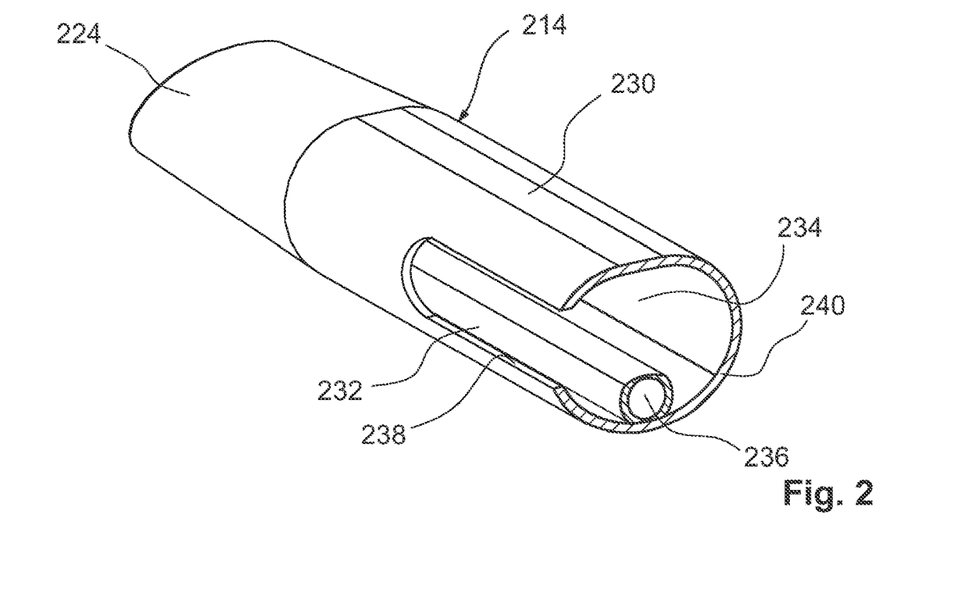
FIG. 2: is a sectional view through the shaft of the instrument as shown in FIG. 1.

FIG. 2 illustrates a section through the shaft 214, wherein the sectional plane in FIG. 1 is indicated by a dashed block II-II. The spatula 212 is formed by an outer tube 230 with compressed cross-section and/or approximately oval cross section and an inner tube 232. The inner tube 232 comprises an approximately circular inner section. The inner tube 232 is partially flattened at the circumference. The outer tube 230 and the inner tube 232 are originally separate parts, which are joined together. The flattening of the inner tube 232 is at least sectionally adapted to an inner contour of the outer tube 230. Thus the inner tube 232 preferably lies flat (not only with line contact) against the inner wall of the outer tube 230. Between the respective walls of the outer tube 32 and the inner tube 132, pointed grooves are formed, which increases the cleaning effort.

The outer tube 230 (reduced by the space required by the inner tube 232) forms a first channel 234. Through the first channel 234, further instruments can be inserted into the interior of the body. In this way, biopsies can be performed, for example. The inner tube 232 forms a second channel 236. By way of example, the second channel 236 accommodates a lens assembly, an image sensor, an illumination unit, etc. Therefore the second channel 236 may also be referred to as the observation channel. Accordingly, the first channel 234 may also be referred to as the instrument channel.

In the outer tube 230, there is formed a longitudinally extending slot 238, which extends from the proximal end 226 towards the distal end 224. However, the slot does not extend completely longitudinally through the outer tube 230 and/or the shaft 214.

Overall, the outer tube 230 and the inner tube 232 are arranged one inside the other, resulting in the cross section 240 illustrated in FIG. 2. Such a cross-sectional shape based on two tube bodies is hardly feasible with a one-piece conventional manufacturing, at best with a great deal of effort.

With reference to FIGS. 3 to 12, an approach to the one-piece design of shafts of such and similar instruments for providing access to the interior of the body is illustrated.

Figures 3, 4:
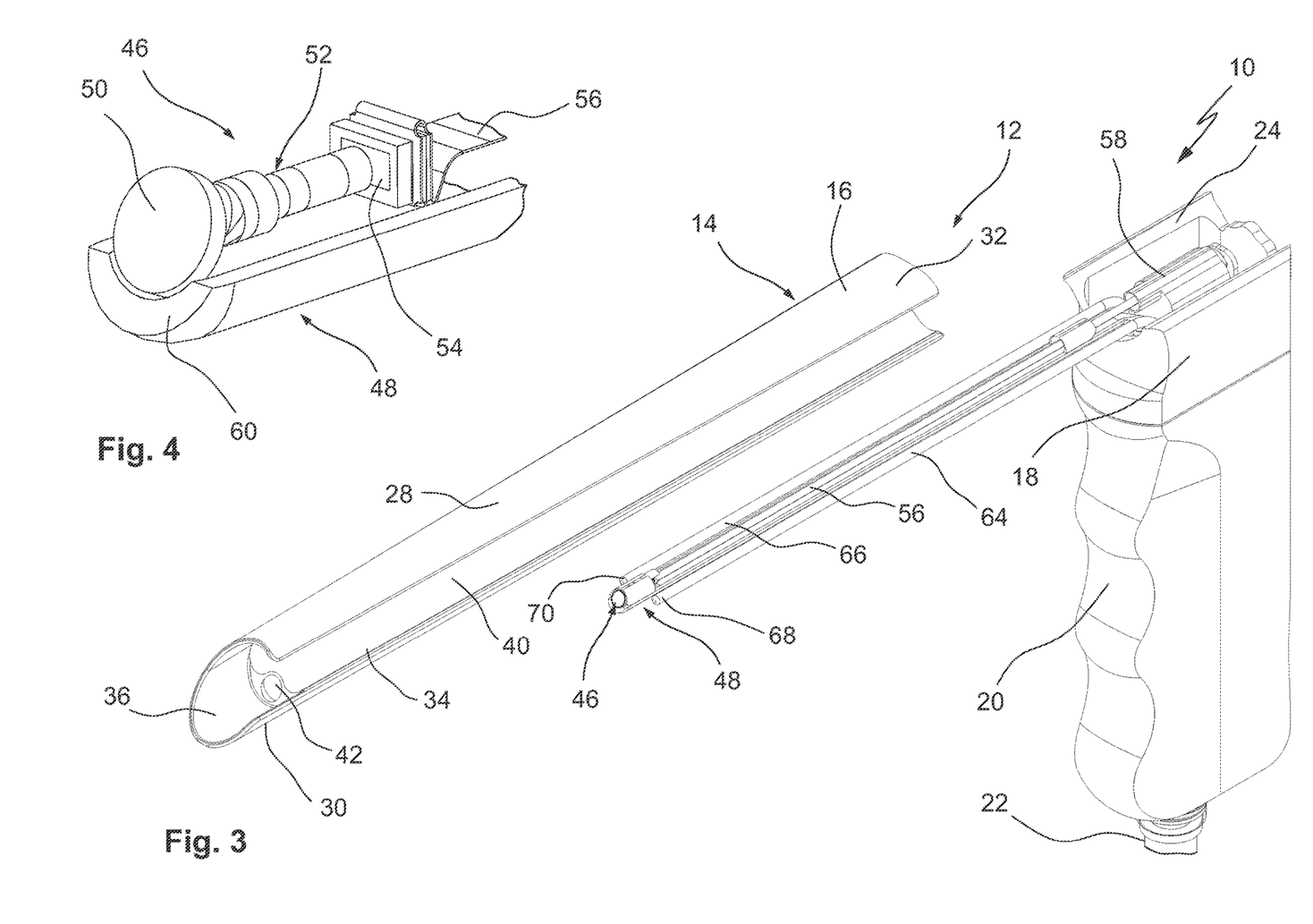
FIG. 3: is a partially exploded perspective view of an embodiment of a medical instrument in the form of a video-mediastinoscope, with a shaft is shown separately for illustrative purposes.
FIG. 4: is an enlarged partial view of the embodiment according to FIG. 3, to illustrate a lens assembly of the instrument.

FIG. 3 shows a perspective frontal view from the distal end of an instrument, which is overall designated by 10. The instrument 10 is exemplarily arranged as a mediastinoscope, for instance as a video mediastinoscope. However, this is not to be understood as a limitation. In general, the instrument 10 can be arranged as an endoscopic instrument.

The instrument 10 comprises a shaft 14, herein referred to as spatula 12. The shaft 14 is essentially, for instance completely, formed by a base body 16. The base body 16 is preferably manufactured in one piece (integral). Here, additive manufacturing methods are suitable. By way of example, the base body 16 is made from a stainless steel that is suitable for medical applications.

The shaft 14 is connected to a handle 20 via a connecting piece 18. The handle 20 is arranged as a hand grip in the exemplary embodiment shown. The handle 20 in the exemplary embodiment is oriented diagonally or transversely to the shaft 14, roughly in the manner of a pistol grip. This is not to be understood as a limitation, the handle 20 can also be arranged differently. In FIG. 3 a cable outlet/connection on the handle 20 is indicated by 22. The connection 22 forms an interface for the transfer of energy, media, data and the like. The connecting piece 18 is welded to the shaft 14, by way of example. In principle, it is also conceivable to design the connecting piece 18 together with the shaft 14 in one piece. A seat 24 for the shaft 14 is formed on the connecting piece 18.

The shaft 14 and/or the base body 16 forming the shaft 14 comprise a cladding 28 that defines a circumferential region and/or a circumferential wall. The base body 16 extends between a distal end 30 and a proximal end 32. The terms distal end 30 and proximal end 32 each refer to a corresponding section of the shaft 14. A (lateral) slot 34 extends between the distal end 30 and the proximal end 32. In the exemplary embodiment shown in FIG. 3, the slot 34 extends over the entire longitudinal extension of the base body 16. A tongue-shaped tip 36 is formed at the distal end 30. The tip 36 is formed by an oblique section 38 (see also FIG. 5) of the base body 16.

The base body 16 forms a first channel 40 and a second channel 42 in the shaft 14. In the exemplary embodiment, the first channel 40 comprises a much larger cross section than the second channel 42. The second channel 42 is formed in a peripheral area of the first channel 40. Both the first channel 40 and the second channel 42 extend through the base body 16. The first channel 40 and the second channel 42 are accordingly arranged as through holes. The first channel 40 forms a passage for instruments to facilitate access to the interior of the body for these instruments.

In the exemplary embodiment, the second channel 42 accommodates an observation optics 46 and an illumination unit 48. In this context, reference is made to the enlarged partial view according to FIG. 4. FIG. 4 illustrates elements that are arranged at the distal end of the second channel 42 in the embodiment shown. By way of example, observation optics 46 comprises a cover glass 50, which forms a distal end, and a lens assembly 52. The lens assembly 52 is arranged between the cover glass 50 and an image sensor 54. The image sensor 54 forms part of an image acquisition unit. The image sensor 54 is exemplarily arranged as an image sensor, for example as a CCD sensor. Image signals acquired by the image sensor 54 can be transmitted as raw data or as data derived from it via a signal line towards the proximal end of the shaft 14. The signal line 56 leads into a housing connector 58. Eventually, the image signals or data derived therefrom can be output via the connection 22.

Accordingly, instrument 10 is suitable for electronic image acquisition (video mediastinoscope and/or video endoscope). In principle, it is also conceivable to provide instrument 10 with a purely optical observation path, wherein the observation path is fed, for example, to an eyepiece for direct observation.

The illumination unit 48, for example, comprises one or more light guides in the form of optical fibers 60. The observation optics 46 (generally the observation path) and the illumination unit 48 (generally the illumination path) share the installation space provided by the second channel 42. Basically, the image sensor 54 and/or generally the image acquisition unit produce a certain amount of waste heat during operation. In addition, a certain amount of heat input into the shaft 14 must also be expected from the illumination unit 48 during operation. This can increase the stress for the patient. Therefore, it is generally desirable to dissipate excess heat generated in the distal region of the shaft 14 towards the proximal end 32 of the shaft 14.

For this purpose, the design according to FIG. 3 provides cooling elements 64, 66, which extend adjacent to the second channel 42 in the base body 16. The cooling element 64 comprises a distal end 68. The cooling element 66 comprises a distal end 70. The distal ends 68, 70 are adjacent to the distal end of the second channel 42. Accordingly, heat can be dissipated from this region via the cooling elements 64, 66.

Figure 5:
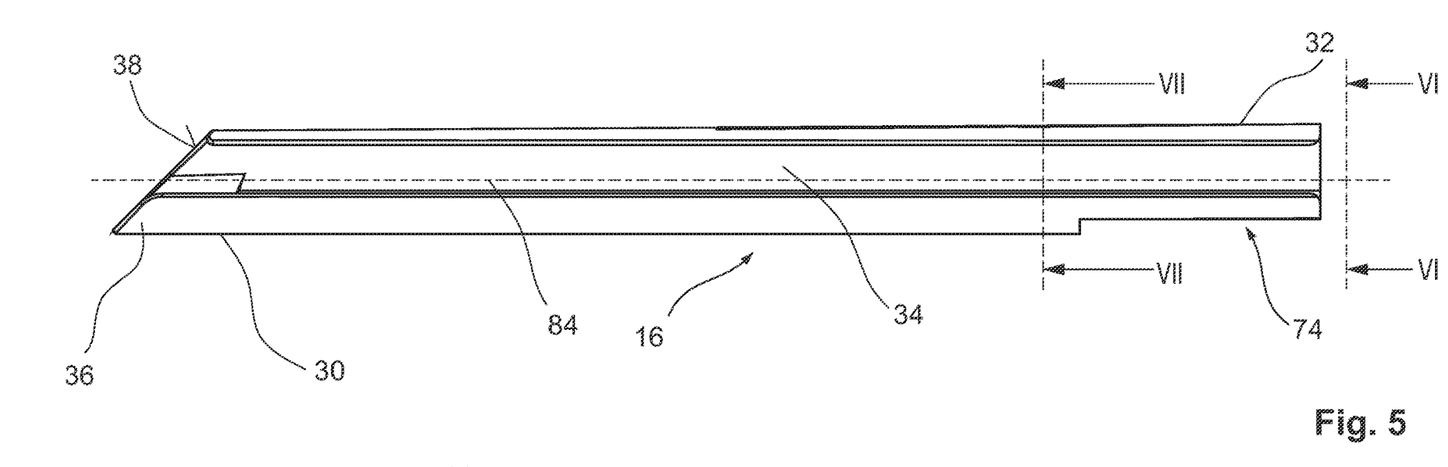
FIG. 5: is a side view of the instrument shaft of the embodiment as shown in FIG. 3.
Figures 8, 9:
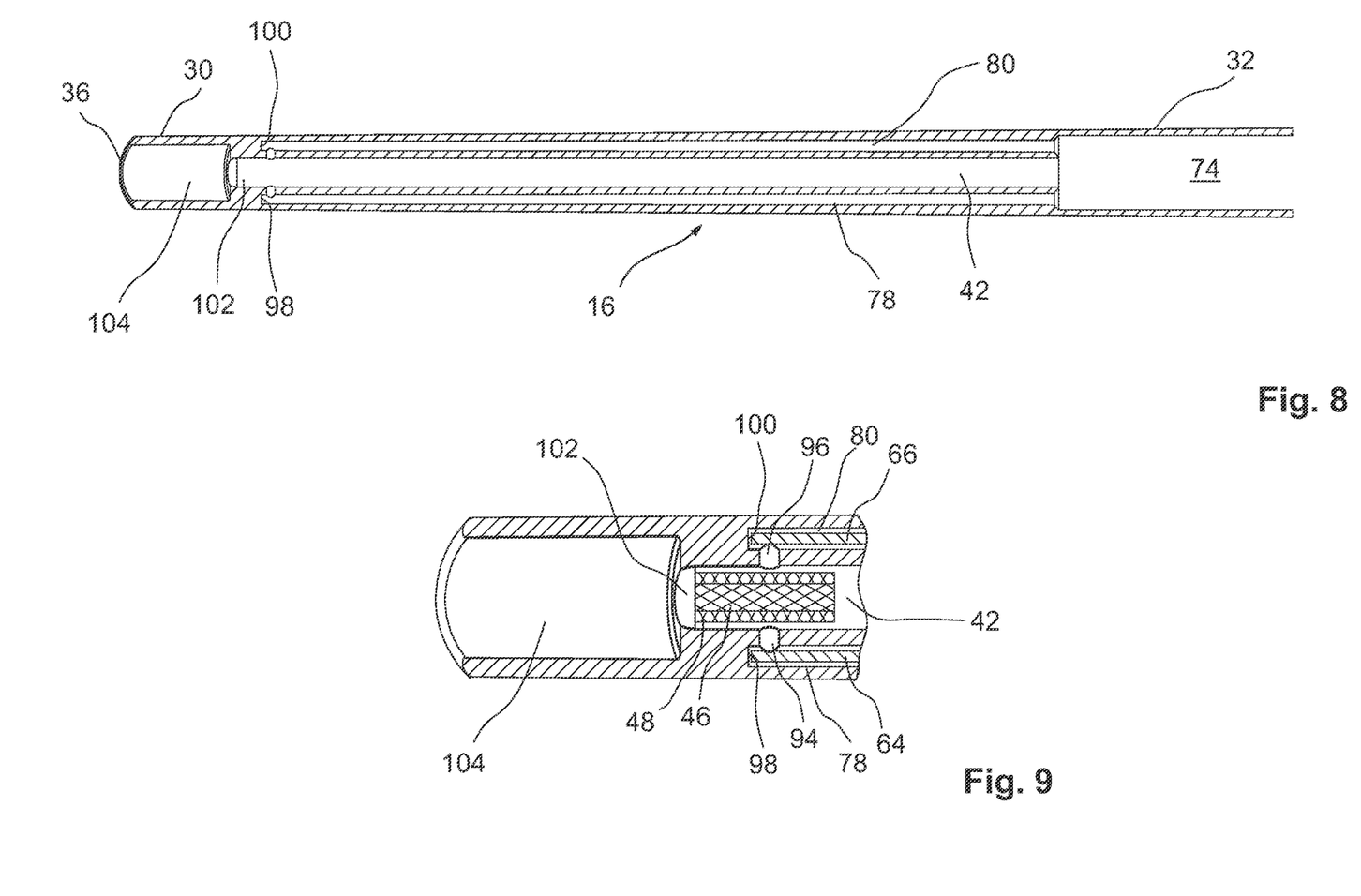
FIG. 8: is a longitudinal section through the instrument shaft as shown in FIG. 5 along line VIII-VIII in FIG. 6.
FIG. 9: is an enlarged partial view of the distal end of the instrument shaft according to FIG. 8.

On the base body 16 and/or on the shaft 14 there is a connection area 74 for the connecting piece 18, see FIG. 5 and FIG. 8. The connection area 74 is adapted to the seat 24 of the connecting piece 18, see FIG. 3.

Figure 6:
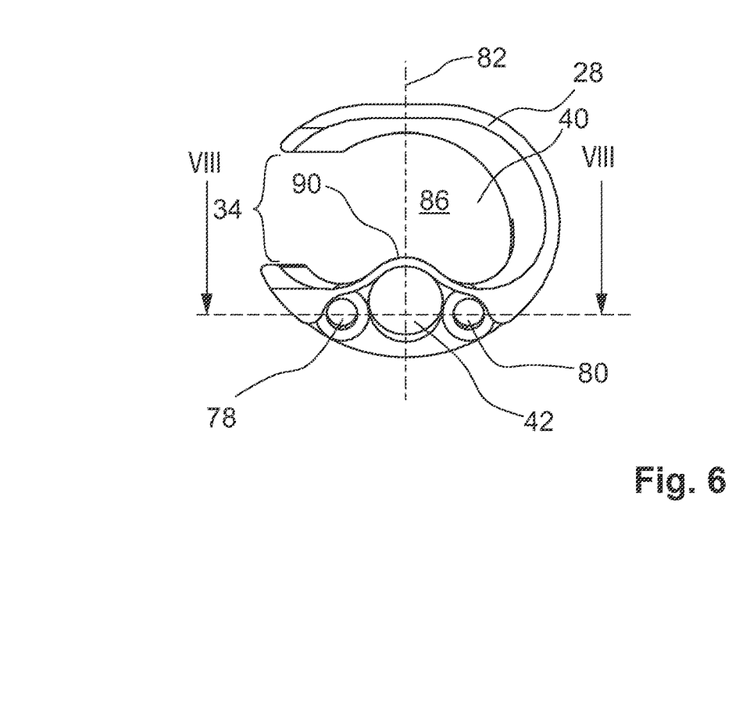
FIG. 6: is a rear view of the instrument shaft as shown in FIG. 5.
Figure 7:
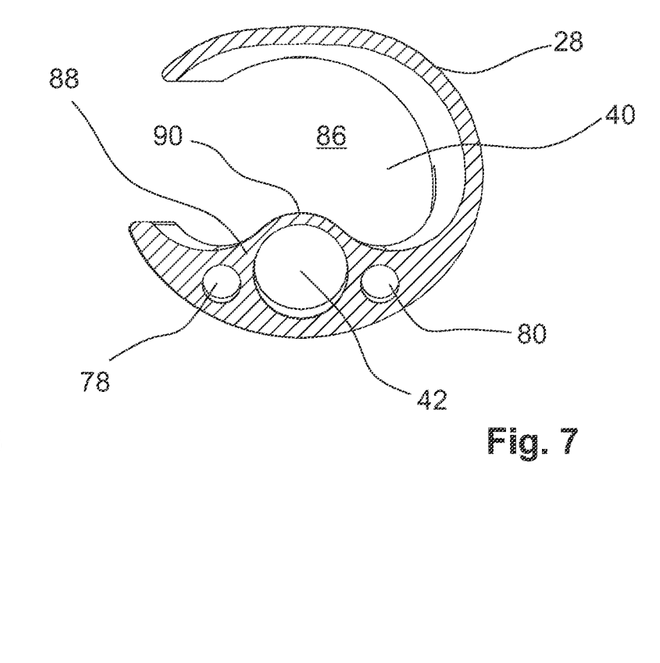
FIG. 7: is a section through the instrument shaft as shown in FIG. 5 along line VII-VII in FIG. 5.

The cooling elements 64, 66 illustrated in FIG. 3 are arranged in secondary channels 78, 80 in the base body 16, the design of which is illustrated below with reference to FIGS. 5-9. FIG. 5 shows a longitudinal side view of the base body 16 on the side, where the slot 34 is located. In FIG. 5, a line VI-VI illustrates the orientation of the view as shown in FIG. 6. Furthermore, a line VII-VII in FIG. 5 illustrates the orientation of the view as shown in FIG. 7. Furthermore, a line VIII-VIII in FIG. 6 illustrates the orientation of the view as shown in FIG. 8. An overview of FIGS. 6-8 shows the basic design and arrangement of the secondary channels 78, 80 in the base body 16.

In FIG. 6, the position of a longitudinal central plane 82 through the shaft 14 and/or the base body 16 is illustrated. FIG. 5 also illustrates a longitudinal axis 84 of the shaft 14. The longitudinal axis 84 defines a longitudinal extension of the shaft 14. However, the shaft 14 and/or its base body 16 are not strictly rotationally symmetrical to the longitudinal axis 84. The longitudinal axis 84 extends through the longitudinal central plane 82.

The secondary channels 78, 80 are arranged symmetrically to the longitudinal central plane 82 in the exemplary embodiment. The second channel 42 is located between the two secondary channels 78, 80. A longitudinal axis (not shown) of the second channel 42 extends through the longitudinal central plane 82. The longitudinal axes (not shown) of the secondary channels 78, 80 together form a plane that is basically perpendicular to the longitudinal central plane 82. The adjacent arrangement of the secondary channels 78, 80 in relation to the second channel 42 allows efficient heat dissipation.

FIG. 6 and FIG. 7 also illustrate a resulting cross section 86 of the first channel 40. The first channel 40 comprises a kidney-shaped cross section 86. The longer main axis of the cross-section 86 is oriented perpendicular to the longitudinal central plane 82. The shorter main axis of the cross-section 86 coincides with the longitudinal central plane 82.

The kidney-shaped cross section 86 comprises a concave "dent", which creates sufficient space within the cladding 28 surrounding the first channel 40 for the integration of the second channel 42 and the secondary channels 78, 80. Nevertheless, the kidney-shaped cross section 86 is formed with soft, smooth transitions, for instance with tangential transitions and without narrow, sharp inner edges. This simplifies the cleaning or preparation of the shaft 14.

In the respective region of the cladding 28, in which the second channel 42 is formed, a thickening 88 with a (convex) elevation 90 inwards into the first channel 40 is provided. In this way, the concave section of the kidney-shaped cross-section 86 is formed. The thickening 88 thus provides sufficient wall thickness for the second channel 42. Since smooth transitions are desired at the inner contour, which forms the first channel 40 and its cross section 86, there is sufficient space on both sides of the second channel 42 to form the two secondary channels 78, 80 for heat dissipation in addition to the second channel 42. This additional function is therefore not bought at the expense of installation space. On the contrary, filling up potential inner edges, which can be problematic during cleaning, results in further potential advantages.

The cross section through the base body 16 shown in FIG. 7 illustrates that a favorable moment of resistance is achieved in the region of the thickening 88, so that the base body 16 is overall sufficiently stiff. This enables a continuous design of the slot 34, see FIG. 5.

In the exemplary embodiment shown, the shaft 14 is slightly tapered from the proximal end 32 towards the distal end 30. This may have the effect that the longitudinal axes of the channels 40, 42, 78, 80 do not necessarily have to be strictly parallel to each other. At least a slight tapering between the channels 40, 42, 78, 80 is conceivable, which is adapted to the taper of the shaft 14. Nevertheless, designs with strictly parallel orientation of the channels 40, 42, 78, 80 are also conceivable.

With additional reference to the sectional view according to FIG. 8 and the additional detailed view of the distal end 30 according to FIG. 9, the functional coupling between the channels 42, 78, 80 is further elucidated. A connection channel 94 is provided between the secondary channel 78 and the second channel 42. Similarly, a connection channel 96 is provided between the secondary channel 80 and the second channel 42. The connection channels 94, 96 form a cross connection between the secondary channels 78, 80 and the second channel 42.

The secondary channel 42 extends through the base body 16 and thus connects the distal end 30 and the proximal end 32, whereas the secondary channels 78, 80 are arranged as blind holes and/or blind holes—at least when viewed axially. This design is illustrated by the reference signs 98, 100, which denote the respective blind holes at the distal end of the secondary channels 78, 80. In contrast, the secondary channel 42 comprises a passage 102, which opens into a trough 104 at the distal end 30 of the base body 16. The trough 104 can also be referred to as the outlet of the first channel 40.

The connecting channels 94, 96 optimize heat dissipation, since heat can be dissipated in a targeted manner from the distal end of the second channel 42 to the cooling elements 64, 66 in the secondary channels 78, 80 via the connecting channels 94, 96. Via the connection channels 94, 96, the secondary channels 78, 80 are coupled with a region of the second channel 42, in which increased heat generation can be expected.

In order to improve heat dissipation, it is conceivable to bridge the connecting channels 94, 96 and generally the "gap" between the cooling elements 64, 66 and the observation optics 46 with the image sensor 54 and/or the illumination unit 48 using suitable materials (heat-conducting paste or similar). In general, the connecting channels 94, 96 can be filled with a substance with high thermal conductivity.

The connecting channels 94, 96 cannot be produced with conventional, material-removing manufacturing processes or only at great expenses. By way of example, if the base body 16 is to be designed as a single piece, conventional manufacturing of the connecting channels 94, 96 is almost impossible. On the other hand, additive manufacturing allows such an unconventional design.

Figure 10:
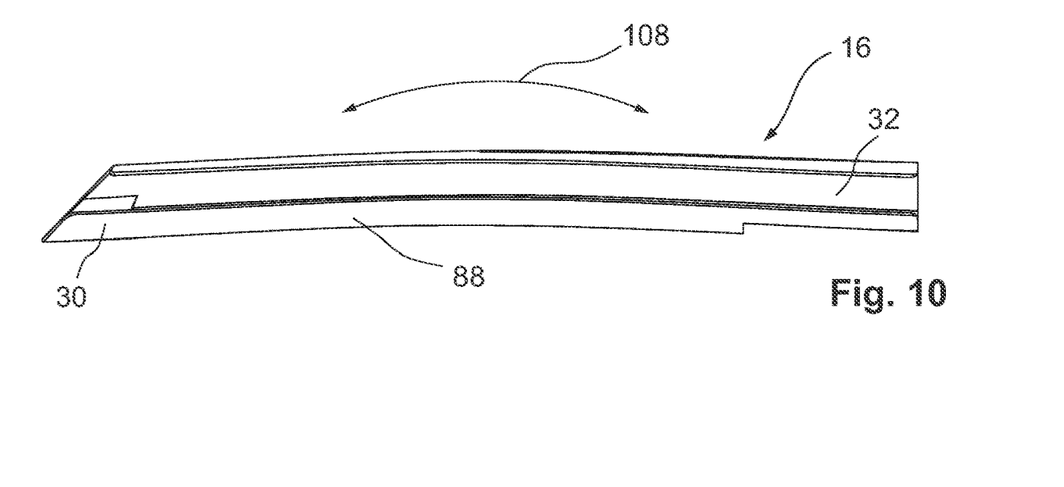
FIG. 10: is a side view of an embodiment of an instrument shaft with manufacturing-related distortion.
Figure 11:
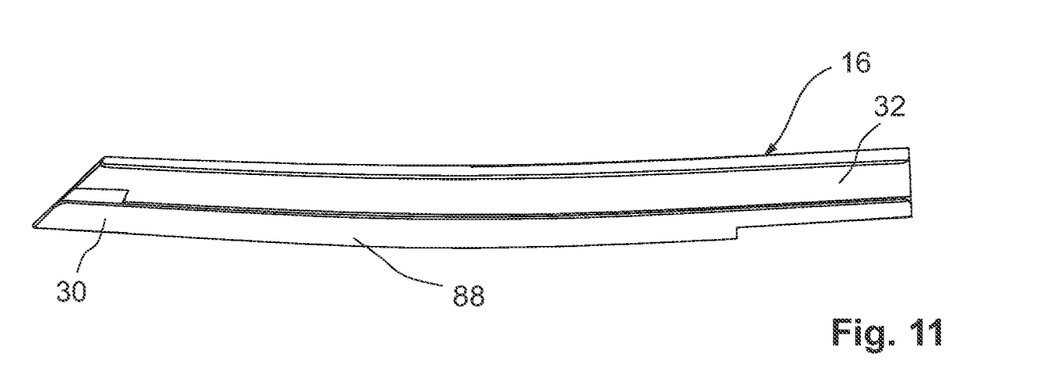
FIG. 11: is a side view of a data model of the instrument shaft according to FIG. 10 with anticipated distortion.
Figure 12:
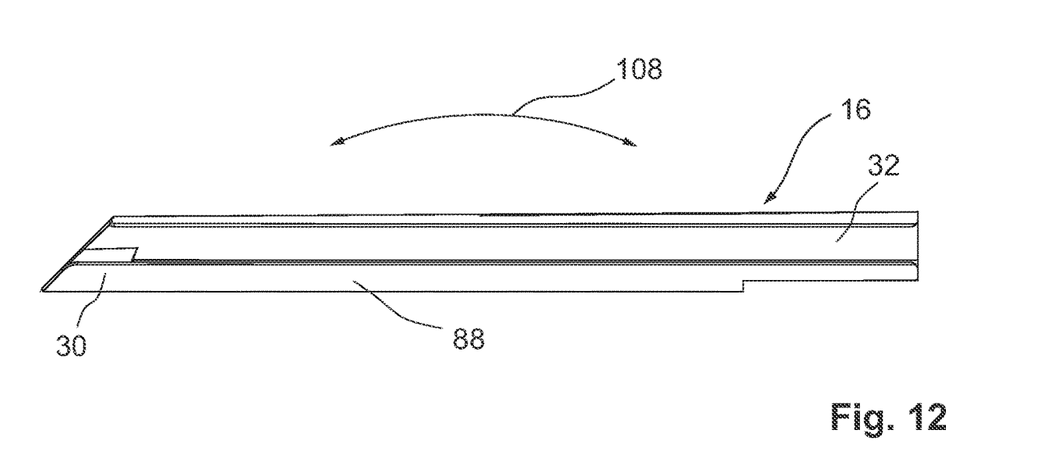
FIG. 12: is a side view of an instrument shaft with manufacturing-related distortion, which has been manufactured based on the data model according to FIG. 11.

With reference to FIGS. 10-12, simplified longitudinal side views of the base body 16 are used to illustrate an approach to manage manufacturing-related distortion in the additive manufacturing of the base body 16. In additive manufacturing, a certain amount of deformation (distortion/warpage) of the components is to be expected. By way of example, components with inhomogeneous/uneven material distribution must be expected to distort due to corresponding inhomogeneous shrinkage. It is understood that the curvature and/or degree of warpage of the components shown in FIGS. 10-12 may be exaggerated for illustrative purposes.

FIG. 10 shows a resulting distortion in the base body 16, if the data embodiment (CAD model), on which the manufacturing is based, is ideally straight, cf. the illustration in FIG. 5 with the straight longitudinal axis 84. It is understood that a distortion can be present not only in the plane shown, but also in a plane perpendicular to the view plane.

The cause of the distortion is, for example, the accumulation of material forming the thickening 88, see also FIG. 7. If this region tends to "shrink" more than thinner regions of the cladding 28, then the curved shape shown in FIG. 10 can result after manufacturing and cooling. The tendency of the deformation is illustrated by the curved double arrow marked 108.

In order to avoid such deformations, it is therefore proposed that the distortion be accounted for in the data embodiment (CAD model, on which the manufacturing is based). For example, the data embodiment used for the manufacture corresponds to the shape shown in FIG. 11. In other words, the base body 16 in the data embodiment is curved in the opposite direction to the expected distortion-induced curvature (see FIG. 10). After manufacturing and cooling in the exemplary embodiment, this now results in the design shown in FIG. 12. Ideally, the unavoidable bending then leads to a straight or almost straight state starting from the opposite curvature in FIG. 11. Cf. again the double arrow 108 that illustrates the tendency of the manufacturing-related deformation.

Figure 13:
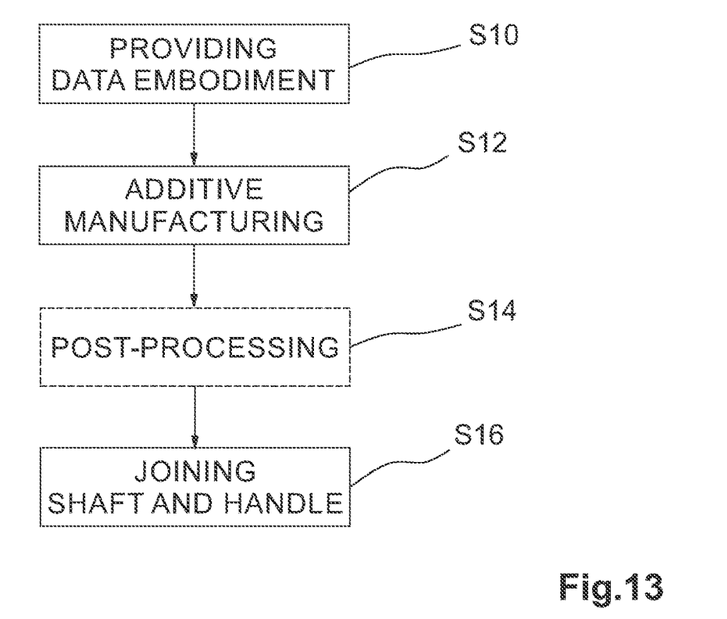
FIG. 13: is a block diagram illustrating an embodiment of a method for manufacturing a medical instrument.

With reference to FIG. 13, a block diagram is used to illustrate an exemplary design of a method for manufacturing a component for a medical instrument, for example a shaft-shaped spatula with several channels. The method comprises a step S10, which includes providing a (CAD) data embodiment. The data embodiment can be generated based on a CAD model. The data embodiment is fed directly or indirectly to a system for additive manufacturing, where it is used to make the base body, which forms the shaft, in one piece and integrally, step S12. By way of example, additive manufacturing is carried out by processing a metal material, for example a stainless steel powder. The base body comprises at least one first channel, one second channel and at least one secondary channel, which is adjacent to the second channel and connected to it. Preferably, the base body is produced in this way with little or no post-processing.

An optional step S14 can follow. The step S14 includes a post-processing, for example a surface processing of at least one of the channels by means of flow machining. In this way, a desired surface quality can be produced in the second channel or the first channel, for example.

Finally a step S16 follows, which includes joining the shaft with a handle. This can be done with the interposition of a connector. In this way, an instrument with a complex shaft design can be produced in just a few steps. This may involve instruments in the form of mediastinoscopes, or endoscopic instruments in general.

Figure 14:
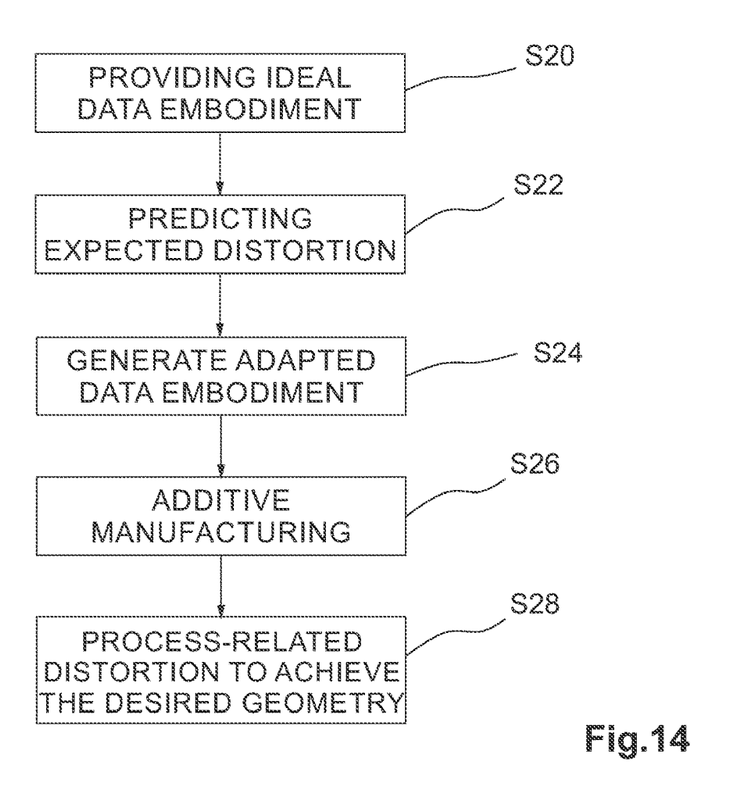
FIG. 14: is a block diagram illustrating an approach for accounting for manufacturing-related distortion in a method of manufacturing a medical instrument.

With reference to FIG. 14, a block diagram is used to illustrate another exemplary design of a method for producing a component for a medical instrument, for example a shaft-shaped spatula with several channels. The embodiment shown in FIG. 14 supplements the method illustrated with reference to FIG. 13. The method steps according to FIG. 14 are generally concerned with the manufacture of the instrument, for example of its shaft, with compensation of manufacturing-related distortion.

The method includes a step S20, which includes providing an ideal data embodiment. This is, for example, a CAD model, which does not yet take into account any possible distortion. In other words, if there were no distortion or other deformations during manufacturing, a 1:1 implementation of the ideal data embodiment would result in the desired shape.

However, a certain shrinkage and, as a result, a certain amount of distortion has to be expected with additive manufacturing. Therefore, the step S20 is followed by a further step S22, which includes a prediction of the expected distortion. The step S22 can include calculations or simulations, but also tests with real components or combined approaches. Based on the prediction in the step S22, an adapted model of the component, i.e. an adapted data embodiment, is generated and provided in a further step S24. The data embodiment anticipates the expected distortion. In other words, the data embodiment contains a geometry that is curved in the opposite direction to the expected curvature.

Subsequently, in a step S26 the additive manufacture of the component follows, cf. the step S12 in FIG. 13. Immediately after the additive manufacture (and/or even with a time overlap to it) follows a step S28, which contains the process-related shrinkage and the process-related distortion on the real component. Since the manufacturing is based on the adapted model, the step S28 results in a geometry, which largely or completely corresponds to the ideal shape (cf. Step S20).

What is claimed is:

1. A medical instrument configured to provide access to an interior of a body, the instrument comprising:
a shaft having an elongated base body,
wherein the base body extends between a distal end and a proximal end of the shaft, and
a handle that is coupled to the base body of the shaft at the proximal end,
wherein the shaft includes at least a first channel and a second channel that are formed in and extending through the shaft,
wherein the first channel is configured to provide a passage for surgical instruments through the shaft,
an observation optics accommodated in the second channel
wherein the second channel is adjacent to at least one auxiliary cooling channel, and the at least one auxiliary cooling channel is configured to provide cooling to the observation optics via a cooling rod disposed in the at least one auxiliary cooling channel that extends at least from a distal end to a proximal end of the at least one auxiliary cooling channel, wherein the second channel is connected to the at least one cooling channel by a connecting channel located adjacent to the observation optics,
wherein the first channel, the second channel and the at least one auxiliary cooling channel are formed in the base body, and
wherein the base body of the shaft is an integrally formed one-piece design formed through additive manufacturing.

2. The instrument of claim 1,
wherein the base body is slotted along its longitudinal extension.

3. The instrument of claim 1,
wherein the second channel is adapted to accommodate an illumination unit in addition to the observation optics.

4. The instrument of claim 1,
further comprising a connection channel that is formed in the shaft and that connects the second channel and the at least one auxiliary cooling channel.

5. The instrument of claim 4,
wherein the connection channel is arranged in or adjacent to a distal end region.

6. The instrument of claim 1,
wherein the at least one auxiliary cooling channel is arranged as a blind hole and closed at the distal end of the shaft.

7. The instrument of claim 1,
wherein the cooling rod extends into the handle.

8. The instrument of claim 1,
wherein two auxiliary cooling channels are provided, and
wherein the second channel is located between the two auxiliary cooling channels that are connecting a distal end region of the second channel to the proximal end.

9. The instrument of claim 1,
wherein the first channel has a kidney-shaped cross section, and
wherein the second channel is adjacent to a concave section of the kidney-shaped cross-section.

10. The instrument of claim 1,
wherein the second channel is located between the first channel and the handle, when viewed in a longitudinal central plane through the shaft, and
wherein the at least one auxiliary cooling channel is located laterally of the longitudinal central plane through the shaft.

11. The instrument of claim 1,
wherein the base body of the shaft comprises, at its circumferential region that is facing the handle, an accumulation of material, which accommodates the second channel and the at least one auxiliary cooling channel.

12. The instrument of claim 1,
wherein the base body is tapered towards the distal end.

13. The instrument of claim 1,
wherein at the distal end, a tip is formed at the base body.

14. The instrument of claim 1,
wherein the second channel accommodates in its distal end region a lens assembly, which is arranged in front of an image sensor.

15. The instrument of claim 1,
wherein the shaft and the handle form part of a spatula for an endoscopic instrument.

16. The instrument of claim 1, wherein the second channel is connected to at least one of two auxiliary cooling channels by respective connecting channels, and the connecting channels contain a heat-conducting paste.

17. A spatula configured to provide access to an interior of a body for an endoscopic instrument, the spatula comprising:
a shaft having an elongated base body,
wherein the base body extends between a distal end and a proximal end of the shaft, and
a handle that is coupled to the base body of the shaft at the proximal end,
wherein the shaft includes at least a first channel and a second channel that are formed in and extending through the shaft,
wherein the first channel is configured to provide a passage for surgical instruments through the shaft,
an observation optics accommodated in the second channel
wherein the second channel is adjacent to at least one cooling channel,
a cooling rod disposed in the at least one cooling channel, the cooling rod extending at least from a distal end to a proximal end of the at least one cooling channel and configured to provide cooling to the observation optics,
wherein the second channel is connected to the at least one auxiliary cooling channel by a connecting channel located adjacent to the observation optics,
wherein the first channel, the second channel and the at least one cooling channel are formed in the base body, and
wherein the base body of the shaft is an integrally formed monolithic design formed by an additive manufacturing process.

18. The spatula of claim 17, wherein the second channel is connected to at least one of two cooling channels by respective connecting channels, and the connecting channels contain a heat-conducting paste.

19. An endoscopic instrument configured to provide access to an interior of a body, the instrument comprising:
a shaft having an elongated base body, the base body extending between a distal end and a proximal end of the shaft, wherein the shaft includes at least a first channel and a second channel that are formed in and extend through the shaft,
wherein:
the first channel is configured to provide a passage for surgical instruments through the shaft,
the second channel is adapted to accommodate observation optics,
the second channel is connected, via a connecting channel, to at least one auxiliary cooling channel that houses a cooling rod that is configured to provide cooling to the observation optics which are located in the second channel, the at least one auxiliary cooling channel terminating in a blind hole at the distal end, the cooling rod extending at least from the distal end to a proximal end of the at least one auxiliary cooling channel, the second channel being connected to the at least one auxiliary cooling channel by a connecting channel located adjacent to the observation optics,
the first channel, the second channel and the at least one auxiliary cooling channel are formed in the base body, and
the base body of the shaft is an integrally formed monolithic design formed by an additive manufacturing process.

20. The instrument of claim 19, wherein the second channel is connected to at least one of two auxiliary cooling channels by respective connecting channels, and the connecting channels contain a heat-conducting paste.

* * * * *